US006268136B1

(12) United States Patent
Shuber et al.

(10) Patent No.: US 6,268,136 B1
(45) Date of Patent: Jul. 31, 2001

(54) METHODS FOR STOOL SAMPLE PREPARATION

(75) Inventors: Anthony P. Shuber, Milford, MA (US); Stanley N. Lapidus, Bedford, NH (US); Gail E. Radcliffe, Worcester, MA (US)

(73) Assignee: Exact Science Corporation, Maynard, MA (US)

( * ) Notice: Subject to any disclaimer, the term of this patent is extended or adjusted under 35 U.S.C. 154(b) by 0 days.

(21) Appl. No.: 09/198,083

(22) Filed: Nov. 23, 1998

Related U.S. Application Data

(63) Continuation-in-part of application No. 08/876,638, filed on Jun. 16, 1997, now abandoned.

(51) Int. Cl.[7] .............................. C12Q 1/68; C12P 19/34
(52) U.S. Cl. ......................... 435/6; 435/91.1; 435/91.2; 436/63; 436/64
(58) Field of Search ........................... 435/6, 91.1, 91.2; 436/63, 64

(56) References Cited

U.S. PATENT DOCUMENTS

| 4,101,279 | 7/1978 | Aslam . | |
|---|---|---|---|
| 4,309,782 | 1/1982 | Paulin . | |
| 4,333,734 | 6/1982 | Fleisher . | |
| 4,358,535 | 11/1982 | Falkow et al. ............................ | 435/5 |
| 4,445,235 | 5/1984 | Slover et al. . | |
| 4,535,058 | 8/1985 | Weinberg et al. . | |
| 4,578,358 | 3/1986 | Oksman et al. ....................... | 436/66 |
| 4,683,195 | 7/1987 | Mullis et al. . | |
| 4,705,050 | 11/1987 | Markham . | |
| 4,735,905 | 4/1988 | Parker . | |
| 4,786,718 | 11/1988 | Weinberg et al. . | |
| 4,857,300 | 8/1989 | Maksem . | |
| 4,871,838 | 10/1989 | Bos et al. . | |
| 4,935,342 | 6/1990 | Seligson et al. ......................... | 435/6 |
| 4,981,783 | 1/1991 | Augenlicht . | |
| 4,982,615 | 1/1991 | Sultan et al. . | |
| 5,087,617 | 2/1992 | Smith . | |
| 5,126,239 | 6/1992 | Livak et al. . | |
| 5,137,806 | 8/1992 | LeMaistre et al. . | |
| 5,149,506 | 9/1992 | Skiba et al. . | |
| 5,196,167 | 3/1993 | Guadagno et al. . | |
| 5,200,314 | 4/1993 | Urdea ...................................... | 435/6 |

(List continued on next page.)

FOREIGN PATENT DOCUMENTS

| 11325/95 | 4/1996 | (AU) . |
| 195 30 132 | 2/1997 | (DE) . |
| 0 284 362 A2 | 9/1988 | (EP) . |
| 0 284 362 A3 | 9/1988 | (EP) . |
| 0 337 498 A2 | 10/1989 | (EP) . |
| 0 390 323 A2 | 10/1990 | (EP) . |
| 0 390 323 A3 | 10/1990 | (EP) . |
| 0 391 565 | 10/1990 | (EP) . |
| 0 407 789 A1 | 1/1991 | (EP) . |
| 0 407 789 B1 | 1/1991 | (EP) . |
| 0 608 004 A2 | 7/1994 | (EP) . |
| 0 259 031 B1 | 11/1994 | (EP) . |
| 0 648 845 A2 | 4/1995 | (EP) . |
| 0 664 339 A1 | 7/1995 | (EP) . |
| 0664339 | 7/1995 | (EP) . |
| WO 90/09455 | 8/1990 | (WO) . |
| WO 92/13103 | 8/1992 | (WO) . |

(List continued on next page.)

OTHER PUBLICATIONS

Watson et al. (Sep. 1994) "Isolation of Differentially Expressed Sequence Tags From Human Breast Cancer," *Cancer Res.* 54(17):4598–4602.

Chen et al., (Jul. 1996). "Detection of Single–Base Mutations by a Competitive Mobility Shift Assay", *Analytical Biochemistry*, vol. 239, No. 1, pp. 61–69.

Lefrere et al., (Oct. 1998) "Screening Blood Donations for Viral Genomes: Multicenter Study of Real–Time Simulation Using Pooled Samples on the Model of HCV RNA Detection," *Transfusion*, vol. 38, pp. 915–923.

Morandi et al., (Jun. 1998) "Detection of HIV Type 1 RNA in Pools of Sera Negative for Antibiotics to HIV–1 and HIV–2," *J. of Clinical Microbiology*, vol. 36, No. 6, pp. 1534–1538.

Pacek et al. (May 1993) "Determination of Allele Frequencies at Loci with Length Polymorphism by Quantitative Analysis of DNA Amplified from Pooled Samples," *PCR Methods and Applications*, vol. 2, No. 4, pp. 313–317.

Ruzicka et al., (1992) "Apolipoprotein Allele Specific PCR: Large–Scale Screening of Pooled Blood Samples," *J. of Lipid Research*, vol. 33, pp. 1563–1567.

Shaw et al., (1998) "Allele Frequency Distribution in Pooled DNA Samples, Applications to Mapping Complex Disease Genes," *Genome Research*, vol. 8, pp. 111–123.

Walton et al., (1997) "A PCR–Based Method for Detecting Rare Genotypes in Large Samples of Individuals," *Mol. Ecology*, vol. 6, No. 2, pp. 195–197.

Samiotaki et al. (1994), "Dual–Color Detection of DNA Sequence Variants by Ligase–Mediated Analysis," *Genomics* 20:238–42.

Rinaldy et al. (1988), "Gene Cloning Using cDNA Libraries in a Differential Competition Hybridization Strategy: Application to Cloning XP–A Related Genes," *DNA* 7(8):563–70.

(List continued on next page.)

Primary Examiner—Kenneth R. Horlick
(74) *Attorney, Agent, or Firm*—Testa, Hurwitz & Thibeault LLP (57) ABSTRACT

The present invention provides methods for the preparation of stool samples to increase the yield of relevant DNA, and further provides methods for isolating and analyzing target DNA for characteristics indicative of colorectal cancer. Methods for screening patients for the presence of cancerous or pre-cancerous colorectal lesions are also provided.

48 Claims, 3 Drawing Sheets

U.S. PATENT DOCUMENTS

| | | |
|---|---|---|
| 5,248,671 | 9/1993 | Smith . |
| 5,272,057 | 12/1993 | Smulson et al. . |
| 5,302,509 | 4/1994 | Cheeseman . |
| 5,330,892 | 7/1994 | Vogelstein et al. . |
| 5,331,973 | 7/1994 | Fiedler et al. ......................... 128/760 |
| 5,348,855 | 9/1994 | Dattagupta et al. . |
| 5,352,775 | 10/1994 | Albertsen et al. . |
| 5,362,623 | 11/1994 | Vogelstein et al. . |
| 5,369,004 | 11/1994 | Polymeropoulos et al. . |
| 5,378,602 | 1/1995 | Polymeropoulos et al. . |
| 5,380,645 | 1/1995 | Vogelstein . |
| 5,380,647 | 1/1995 | Bahar . |
| 5,382,510 | 1/1995 | Levine et al. . |
| 5,409,586 | 4/1995 | Kamahori et al. . |
| 5,416,025 | 5/1995 | Krepinsky et al. ..................... 436/63 |
| 5,458,761 | 10/1995 | Kamahori et al. . |
| 5,463,782 | 11/1995 | Carlson et al. . |
| 5,466,576 | 11/1995 | Schulz et al. . |
| 5,468,610 | 11/1995 | Polymeropoulos et al. . |
| 5,468,613 | 11/1995 | Erlich et al. . |
| 5,482,834 | 1/1996 | Gillespie .................................. 435/6 |
| 5,489,508 | 2/1996 | West et al. . |
| 5,492,808 | 2/1996 | de la Chapelle et al. . |
| 5,496,470 | 3/1996 | Lenhart . |
| 5,506,105 | 4/1996 | Haydock .................................. 435/6 |
| 5,508,164 | 4/1996 | Kausch et al. . |
| 5,512,441 | 4/1996 | Ronal . |
| 5,514,547 | 5/1996 | Balazs et al. . |
| 5,527,676 | 6/1996 | Vogelstein et al. . |
| 5,532,108 | 7/1996 | Vogelstein . |
| 5,538,851 | 7/1996 | Fach et al. ............................... 435/6 |
| 5,559,014 | 9/1996 | Estes et al. ......................... 435/91.2 |
| 5,580,729 | 12/1996 | Vogelstein . |
| 5,589,335 | 12/1996 | Kearney et al. .......................... 435/6 |
| 5,612,473 | 3/1997 | Wu et al. ............................ 536/25.42 |
| 5,635,352 | 6/1997 | Urdea et al. .............................. 435/6 |
| 5,670,325 | 9/1997 | Lapidus et al. ........................... 435/6 |
| 5,688,643 | 11/1997 | Oka et al. ................................. 435/6 |
| 5,709,998 | 1/1998 | Kinzler et al. . |
| 5,741,650 | 4/1998 | Lapidus et al. ........................... 435/6 |
| 5,759,777 | 6/1998 | Kearney et al. .......................... 435/6 |
| 5,830,665 | 11/1998 | Shuber et al. . |
| 5,846,710 | 12/1998 | Bajaj ....................................... 435/6 |
| 5,856,104 | 1/1999 | Chee et al. ............................... 435/6 |
| 5,888,778 | 3/1999 | Shuber ................................ 435/91.1 |
| 5,910,407 * | 6/1999 | Vogelstein et al. ....................... 435/6 |
| 5,928,870 | 7/1999 | Lapidus et al. . |
| 5,952,178 * | 9/1999 | Lapidus et al. ........................... 435/6 |
| 6,020,137 | 2/2000 | Lapidus et al. . |
| 6,037,465 * | 3/2000 | Hillebrand et al. ................ 536/25.42 |
| 6,100,029 | 8/2000 | Lapidus et al. ........................... 435/6 |
| 6,143,529 * | 11/2000 | Lapidus et al. ...................... 435/91.2 |
| 6,146,828 | 11/2000 | Lapidus ................................... 435/6 |

FOREIGN PATENT DOCUMENTS

| | | |
|---|---|---|
| WO 92/16657 | 10/1992 | (WO) . |
| WO 93/18186 | 9/1993 | (WO) . |
| WO 93/20233 | 10/1993 | (WO) . |
| WO 93/20235 | 10/1993 | (WO) . |
| WO 94/00603 | 1/1994 | (WO) . |
| WO 94/01447 | 1/1994 | (WO) . |
| WO 94/09161 | 4/1994 | (WO) . |
| WO 94/10575 | 5/1994 | (WO) . |
| WO 94/11383 | 5/1994 | (WO) . |
| WO 95/07361 | 3/1995 | (WO) . |
| WO 95/09928 | 4/1995 | (WO) . |
| WO 95/09929 | 4/1995 | (WO) . |
| WO 95/12606 | 5/1995 | (WO) . |
| WO 95/13397 | 5/1995 | (WO) . |
| WO 95/15400 | 6/1995 | (WO) . |
| WO 95/16792 | 6/1995 | (WO) . |
| WO 95/18818 | 7/1995 | (WO) . |
| WO 95/19448 | 7/1995 | (WO) . |
| WO 95/25813 | 9/1995 | (WO) . |
| WO 95/31728 | 11/1995 | (WO) . |
| WO 96/01907 | 1/1996 | (WO) . |
| WO 96/06951 | 3/1996 | (WO) . |
| WO 96/08514 | 3/1996 | (WO) . |
| WO 96/12821 | 5/1996 | (WO) . |
| WO 96/13611 | 5/1996 | (WO) . |
| WO 96/30545 | 10/1996 | (WO) . |
| WO 97/09449 | 3/1997 | (WO) . |
| WO 97/09600 | 3/1997 | (WO) . |
| WO 97/09600A | 3/1997 | (WO) . |
| WO 97/23651 | 7/1997 | (WO) . |
| WO97/25442 | 7/1997 | (WO) . |
| 97/28450 | 8/1997 | (WO) . |
| WO 98/38338 | 9/1998 | (WO) . |
| WO 98/39478 | 9/1998 | (WO) . |
| WO 98/58081 | 12/1998 | (WO) . |
| WO 98/58084 | 12/1998 | (WO) . |
| WO 99/07894 | 2/1999 | (WO) . |
| WO 99/20798 | 4/1999 | (WO) . |
| WO 99/28507 | 6/1999 | (WO) . |
| WO 99/53316 | 10/1999 | (WO) . |
| WO 99/55912 | 11/1999 | (WO) . |
| WO 99/66077 | 12/1999 | (WO) . |
| WO 00/09751 | 2/2000 | (WO) . |
| WO 00/11215 | 3/2000 | (WO) . |
| WO 00/31298 | 6/2000 | (WO) . |
| WO 00/31303 | 6/2000 | (WO) . |
| WO 00/31305 | 6/2000 | (WO) . |
| WO 00/32820 | 6/2000 | (WO) . |
| WO 00/50640 | 8/2000 | (WO) . |
| WO 00/58514 | 10/2000 | (WO) . |
| WO 00/61808 | 10/2000 | (WO) . |
| WO 00/66005 | 11/2000 | (WO) . |
| WO 00/70096 | 11/2000 | (WO) . |

OTHER PUBLICATIONS

Azhikina et al. (1996), "Factors Affecting the Priming Efficiency of Short Contiguous Oligonucleotide Strings in the Primer Walking Strategy of DNA Sequencing," *DNA Sequence* 6:211–16.

Cohen, Seth P. (1996), Memo: "Human Nucleic Acid Extraction from Stool and Hybridization Protocols" (3 pages).

Hunsaker, William R. et al. (1989), "Use of Reversible Target Capture to Detect Subattomole Quantities of Target Nonradioleotopically in Crude Specimens in One Hour," *Abstracts of the 89th Meeting of the American Society for Microbiology*, D–169, p. 110.

Morrissey, David V. et al. (1989), "Nucleic Acid Hybridization Assays Employing dA–Tailed Capture Probes," *Analytical Biochemistry*, 181:345–359.

Morrissey, David V. et al. (1989), "Nucleic acid hybridization assays employing dA–tailed capture probes. Single capture methods," *Molecular and Cellular Probes*, 3(2):189–207.

Vera–Garcia, M. et al. (1993), "Development and Evaluation of an Instrument Designed to Reproducibly Release Nucleic Acids from Microorganisms," *Abstracts: American Society for Microbiology—93rd General Meeting*, C–217, p. 484.

Gull Laboratories, Inc. (1996) XTRAX DNA Extraction Kit (Information Sheet) pp. 1–3.

Vogelstein et al., "Preparative and Analytical Purification of DNA from Agarose," *Proc. Natl. Acad. Sci. USA*, vol. 76, No. 2 (1979), pp. 615–619.

Pääbo et al., "Mitochondrial DNA Sequences from a 7000–year old Brain," *Nucleic Acids Research*, vol. 16, No. 20 (1988), pp. 9775–9777.

Coll et al., "Evaluation of a Rapid Method of Extracting DNA from Stool Samples for Use in Hybridization Assays," *J. Clin. Microbiol.*, vol. 27, No. 10 (10/89), pp. 2245–2248.

Boom et al., "Rapid and Simple Method for Purification of Nucleic Acids," *J. Clin. Microbiol.*, vol. 28, No. 3 (3/90), pp. 495–503.

Walsh et al., "Chelex® 100 as a Medium for Simple Extraction of DNA for PCR–Based Typing from Forensic Material," *Bio Techniques*, vol. 10, No. 4 (1991), pp. 506–513.

Sidransky et al., "Identification of ras Oncogene Mutations in the Stool of Patients with Curable Colorectal Tumors," *Science*, vol. 256 (4/92), pp. 102–105.

Caldas et al., "Detection of K–ras Mutations in the Stool of Patients with Pancreatic Adenocarcinoma and Pancreatic Ductal Hyperplasia," *Cancer Research 54* (7/94), pp. 3568–3573.

Loktionov et al., "Early Detection of Cancer–Associated Gene Alterations in DNA Isolated from Rat Feces During Intestinal Tumor Induction with 1,2–dimethylhydrazine," *Int. Journal of Oncology*, 6:437–445 (1995).

Eguchi et al., "Mutations of the p53 Gene in the Stool of Patients with Resectable Colorectal Cancer," *Cancer Supplement*, vol. 77, No. 8 (4/96), pp. 1707–1710.

Coombs et al., "A Rapid, Simple, and User–Friendly Method for DNA Extraction from Clinical Stool Samples," *ASM 1996 General Meeting*, May 21, 1996, New Orleans, LA.

Li et al., "Rapid Detection of *Mycobacterium avium* in Stool Samples from AIDS Patients by Immunomagnetic PCR," *J. Clin. Microbiol.*, vol. 34, No. 8 (8/96), pp. 1903–1907.

Supplemental Information, ProCipitate and Cleanascite, LigoChem, Inc., Fairfield, NJ (date unknown).

Echeverria et al., "DNA Hybridization in the Diagnosis of Bacterial Diarrhea," *Clinics in Laboratory Medicine*, vol. 5, No. 3, Sep. 1985, pp. 447–462.

Tompkins et al., "Approaches to the Detection of Enteric Pathogens, Including Campylobacter, Using Nucleic Acid hybridization," *Diagn. Microbiol. Infect. Dis.*, vol. 4, 1986, pp. 715–785.

Olive, "Detection of Enterotoxigenic *Escherichia coli* after Polymerase Chain Reaction Amplification with a Thermostable DNA Polymerase," *Journal of Clinical Microbiology*, vol. 27, No. 2, Feb. 1989, pp. 261–265.

Nollau et al, "Isolation of DNA from Stool and bodily Fluids for PCR Amplification", Biotechniques, vol. 20, No. 5 (May 1996), pp. 784–788.*

Villa et al., *Gastroenterology* 110, pp. 1346–1353, 1996.

Ausubel et al., (1995), *Short Protocols in Molecular Biology*, 3d ed., pp. 2–3, 2–12, 3–30 –3–33.

Blum H.E., (1995) "Colorectal Cancer: Future Population Screening for Early Colorectal Cancer" *European Journal of Cancer*, vol. 31A, pp. 1369–1372.

Bos et al., (May 28, 1987) "Prevalence of ras Gene Mutations in Human Colorectal Cancers," *Nature*, vol. 327, pp. 293–297.

Cave et al., (1994) "Reliability of PCR Directly from Stool Samples: Usefulness of an Internal Standard," *BioTechniques*, vol. 16, No. 5, pp. 809–810.

Charlesworth et al., (Sep. 15, 1994) "The Evolutionary Dynamics of Repetitive DNA in Eukaryotes," *Nature*, vol. 371, pp. 215–220.

Cunningham C. and M.G. Dunlop, (1996) "Molecular Genetic Basis of Colorectal Cancer Susceptibility," *British Journal of Surgery*, vol. 83, pp. 321–329.

Deng et al., (Dec. 20, 1996) "Loss of Heterozygosity in Normal Tissue Adjacent to Breast Carcinomas," *Science*, vol. 274, pp. 2057–2059.

Deuter et al., (1995) "A Method for Preparation of Fecal DNA Suitable for PCR," *Nucleic Acids Research*, vol. 23, No. 18, pp. 3800–3801.

Dib et al., (Mar. 14, 1996) "A Comprehensive Genetic Map of the Human Genome Based on 5,264 Microsatellites," *Nature* vol. 380, pp. 152–154.

Duffy M.J., (1995) "Can Molecular Markers Now be Used for Early Diagnosis of Malignancy?" *Clin. Chem.*, vol. 41, No. 10, pp. 1410–1413.

Enari et al., ( Jan. 1, 1998) "A Caspase–Activated DNase that Degrades DNA During Apoptosis, and its Inhibitor ICAD," *Naure*, vol. 391, pp. 43–50.

Fearon, E.R., (1995) "16 Molecular Abnormalities in Colon and Rectal Cancer," *The Molecular Basis of Cancer*, pp. 340–357.

Gyllensten U. B., Allen M., (1995) "Sequencing of In Vitro Amplified DNA," *Recombinant DNA Methodology II*, (Wu, ed.), pp. 565–578.

Hasegawa et al., (1995) "Detection of K–ras Mutations in DNAs Isolated From Feces of Patients with Colorectal Tumors by Mutant–Allele–Specific Amplification (MASA)," *Oncogene*, vol. 10, pp. 1441–1445.

Honchel et al., (1995) "Genomic Instability in Neoplasia," *Seminars in Cell Biology*, vol. 6, pp. 45–52.

Hoss et al., (Sep. 17, 1992) "Excrement Analysis by PCR" *Scientific Correspondence* pp. 199.

Jessup J.M. and G.E. Gallick, (Sep./Oct. 1992) "The Biology of Colorectal Carcinoma," *Current Problems in Cancer* pp. 263–328.

Jonsson et al., (Jan. 1995) "From Mutation Mapping to Phenotype Cloning," *Proc. Natl. Acad. Sci.*, vol. 92 pp. 83–85.

Lengauer et al., (Dec. 17, 1998) "Genetic Instabilities in Human Cancers," *Nature*, vol. 396, pp. 643–649.

Leong et al., (1993) "Detection of MYCN Gene Amplification and Deletions of Chromosome 1 p in Neuroblastoma by In Situ Hybridization Using Routine Histologic Sections," *Laboratory Investigations*, vol. 69, No. 1, pp. 43–50.

Litia et al., (1992) "Simultaneous Detection of Two Cystic Fibrosis Alleles Using Dual–Label Time–Resolved Fluorometry," *Molecular and Cellular Probes*, vol. 6, pp. 505–512.

Loktionov et al., (Feb., 1998) "Quantitation of DNA from Exfoliated Colonocytes Isolated from Human Stool Surface as a Novel Noninvasive Screening Test for Colorectal Cancer," *Clinical Cancer Research*, vol. 4, pp. 337–341.

Mao L. et al., (Feb. 2, 1996) "Molecular Detection of Primary Bladder Cancer by Microsatellite Analysis," *Science*, vol. 271, pp. 659–662.

Morrissey et al., (May 14–18, 1989) "Novel Hybridization Technique with Subattomole Sensitivity in Specimens" *American Society for Microbiology*, 89$^{th}$ Annual Meeting, Abstract D–168, p. 110.

Myers, R.M., (Feb. 12, 1993) "The Pluses of Subtraction," *Science*, vol. 259, pp. 942–943.

Naber S. P., (Dec. 1, 1994) "Molecular Pathology—Detection of Neoplasia," *New England Journal of Medicine*, vol. 331, No. 22, pp. 1508–1510.

Nollau, et al., (1996) "Detection of K–ras Mutations in Stools of Patients with Colorectal Cancer by Mutant–Enriched PCR," *Int. J. Cancer*, vol. 66, pp. 332–336.

Orlow I., et al., (Oct. 18, 1995) "Deletion of the p16 and p15 Genes in Human Bladder Tumors *Journal of the National Cancer Institute*, ," vol. 87, No. 20, pp. 1524–1529.

Piao et al., (Sep. 1997) "Relationship between Loss of Heterozygosity of Tumor Suppressor Genes and Histologic Differentiation in Hepatocellular Carcinoma," *Cancer*, vol. 80, No. 5, pp. 865–872.

Raff, M., (Nov. 12, 1998) "Cell Suicide for Beginners," *Nature*, vol. 396, pp. 119–122.

Ravelingien et al., (1995) "Contribution of Molecular Oncology in the Detection of Colorectal Carcinomas," *Acta Gastro–Enterologica Belgica*, vol. 58, pp. 270–273.

Rhyu M. S., (Mar. 6, 1996) "Molecular Mechanisms Underlying Hereditary Nonpolyposis Colorectal Carcinoma," *Journal of the National Cancer Institute*, vol. 88, No. 5, pp. 240–251.

Ridanpaa et al., (1995) "Detection of Loss of Heterozygosity in the p53 Tumor Suppressor Gene Using a PCR–based Assay," *Path. Res. Pract.*, vol. 191, pp. 399–402.

Sanger et al., (Dec. 1977) "DNA Sequencing with Chain–Terminating Inhibitors" *Proc. Natl. Acad. Sci. USA*, vol. 74, No. 12, pp. 5463–5467.

Segel I., (1976), "Double Label Analysis," *Biochemical Calculations*, 2d ed., pp. 373–376.

Smith–Ravin et al., (1995) "Detection of c–Ki–ras Mutations in Faecal Samples from Sporadic Colorectal Cancer Patients," *Gut*, vol. 36, pp. 81–86.

Takeda et al., (1993) "Detection of K–ras Mutation in Sputum by Mutant–Allele–Specific Amplification (MASA)," *Human Mutation*, vol. 2, pp. 112–117.

Thibodeau et al., (May 7, 1993) "Microsatellite Instability in Cancer of the Proximal Colon," *Science*, vol. 260, pp. 816–819.

Vogelstein, B. and Kinzler, K.W., (Aug., 1999) "Digital PCR," *Proc. Natl. Acad. Sci. USA*, vol. 96, pp. 9236–9241.

Wallace et al., (1979) "Hybridization of Synthetic Oligodeoxyribonucleotides to $\phi_x$174 DNA: the Effect of Single Base Pair Mismatch," *Nucleic Acids Research*, vol. 6, No. 11, pp. 3543–3557.

Walsh et al., (Feb. 6, 1992) "Preferential PCR Amplification of Alleles: Mechanisms and Solutions," *PCR Methods and Applications*, pp. 241–250.

Wang et al., (May 15, 1998) "Large–Scale Identification, Mapping, and Genotyping of Single–Nucleotide Olymorphisms in the Human Genome," *Science*, vol. 280, pp. 1077–1082.

Watson et al., "Isolation of Differentiality Expressed Sequence Tags from Human Breast Cancer," *Advances in Brief XP 000576043*, pp. 4598–4602.

Young G.P., and B.H. Demediu, (1992) "The Genetics, Epidemiology, and Early Detection of Gastrointestinal Cancers" *Current Opinion in Oncology*, vol. 4, pp. 728–735.

Metspalu A., "Arrayed Primer Extention (APEX) for Mutation Detection Using Gene–Specific DNA Chips" *European Journal of Human Genetics*, vol. 6, No. Sup. 1, 1998, p. PL36 XP000892253 Abstract.

Santagati et al., "Quantitation of low abundance mRNAs in glial cells using different polymerase chain reaction (PCR–)–based methods" *Brain Research Protocols*, vol. 1, 1997, pp. 217–223, XP000892447.

Pharmacia, (1998) *BioDirectory*, pp. 104–109.

Pharmacia, (1991/1992) *Molecular and Cell Biology Catalogue*, pp. 8.3–8.6.

* cited by examiner

5'-GT ACT GGT GGA GTA TTT GAT AGT GTA TTA ACC TTA
TGT GTG ACA TGT TCT AAT ATA GTC ACA TTT TCA TTA TTT

CP1

TTA TTA TAA GGC CTG CTG AAA ATG ACT GAA TAT AAA

A1

CTT GTG GTA GTT GGA GCT GGT GGC GTA GGC AAG AGT GCC

TTG ACG ATA CAG CTA ATT CAG AAT CAT TTT GTG GAC GAA

TAT GAT CCA ACA ATA GAG GTA AAT CTT GTT TTA ATA

TGC ATA TTA CTG GTG CAG GAC CAT TCT TTG ATA CAG ATA

AAG GTT TCT CTG ACC ATT TTC ATG TAC AGA AGT CCT TGC

B1

TAA GA-3'

SEQUENCE LISTING

<160> NUMBER OF SEQ ID NOS:  4

<210> SEQ ID NO 1
<211> LENGTH: 37
<212> TYPE: DNA
<213> ORGANISM: Artficial Sequence
<220> FEATURE:
<221> NAME/KEY: misc_feature
<223> OTHER INFORMATION: Description of Artificial Sequence: CP1 kras
      capture probe

<400> SEQUENCE: 1
gcctgctgaa aatgactgaa tataaacttg tggtagt                              37

<210> SEQ ID NO 2
<211> LENGTH: 19
<212> TYPE: DNA
<213> ORGANISM: Artificial Sequence
<220> FEATURE:
<221> NAME/KEY: misc_feature
<223> OTHER INFORMATION: Description of Artificial Sequence: kras PCR
      Primer A1

<400> SEQUENCE: 2
cctgctgaaa atgactgaa                                                  19

<210> SEQ ID NO 3
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: kras PCR
      primer B1

<400> SEQUENCE: 3
catgaaaatg gtcagagaaa                                                 20

<210> SEQ ID NO 4
<211> LENGTH: 307
<212> TYPE: DNA
<213> ORGANISM: homo sapiens
<220> FEATURE:
<221> NAME/KEY: misc_feature
<223> OTHER INFORMATION: Partial nucleotide sequence of the kras gene

<400> SEQUENCE: 4
gtactggtgg agtatttgat agtgtattaa ccttatgtgt gacatgttct aatatagtca     60
cattttcatt atttttatta taaggcctgc tgaaaatgac tgaatataaa cttgtggtag    120
ttggagctgg tggcgtaggc aagagtgcct tgacgataca gctaattcag aatcattttg    180
tggacgaata tgatccaaca atagaggtaa atcttgtttt aatatgcata ttactggtgc    240
aggaccattc tttgatacag ataaaggttt ctctgaccat tttcatgtac agaagtcctt    300
gctaaga                                                              307

METHODS FOR STOOL SAMPLE PREPARATION

RELATED APPLICATIONS

This application is a continuation-in-part of U.S. application Ser. No. 08/876,638, filed Jun. 16, 1997, abandoned.

FIELD OF THE INVENTION

This invention relates to methods for the early detection of colon cancer in patients, and more particularly to methods for preparing stool samples in order to increase the yield of nucleic acids.

BACKGROUND OF THE INVENTION

Stool samples frequently must be prepared for medical diagnostic analysis. Stool samples may be analyzed for diagnosis of medical conditions ranging from parasitic, bacterial or viral infections to inflammatory bowel disease and colorectal cancer.

Colorectal cancer is a leading cause of death in Western society. However, if diagnosed early, it may be treated effectively by removal of the cancerous tissue. Colorectal cancers originate in the colorectal epithelium and typically are not extensively vascularized (and therefore not invasive) during the early stages of development. Colorectal cancer is thought to result from the clonal expansion of a single mutant cell in the epithelial lining of the colon or rectum. The transition to a highly vascularized, invasive and ultimately metastatic cancer which spreads throughout the body commonly takes ten years or longer. If the cancer is detected prior to invasion, surgical removal of the cancerous tissue is an effective cure. However, colorectal cancer is often detected only upon manifestation of clinical symptoms, such as pain and black tarry stool. Generally, such symptoms are present only when the disease is well established, and often after metastasis has occurred. Early detection of colorectal cancer therefore is important in order to significantly reduce its morbidity.

Invasive diagnostic methods such as endoscopic examination allow for direct visual identification, removal, and biopsy of potentially cancerous growths. Endoscopy is expensive, uncomfortable, inherently risky, and therefore not a practical tool for screening populations to identify those with colorectal cancer. Non-invasive analysis of stool samples for characteristics indicative of the presence of colorectal cancer or precancer is a preferred alternative for early diagnosis, but no known diagnostic method is available which reliably achieves this goal.

Current non-invasive screening methods involve assaying stool samples for the presence of fecal occult blood or for elevated levels of carcinoembryonic antigen, both of which are suggestive of the presence of colorectal cancer. Additionally, recent developments in molecular biology provide methods of great potential for detecting the presence of a range of DNA mutations or alterations indicative of a colorectal cancer. The presence of such mutations can be detected in DNA found in stool samples during various stages of colorectal cancer. However, stool comprises cells and cellular debris from the patient, from microorganisms, and from food, resulting in a heterogeneous population of cells. This makes detection of small, specific subpopulations difficult to detect reliably.

Use of the polymarase chain reaction (PCR) has made detection of nucleic acids more routine, but any PCR is limited by the amount of DNA present in a sample. A minimum amount of material must be present for specific analysis and this limitation becomes more relevant when one seeks to detect a nucleic acid that is present in a sample in small proportion relative to other nucleic acids in the sample, which is often the case when analyzing stool sample for detecting DNA characteristics of colorectal cancer. If a low-frequency mutant strand is not amplified in the first few rounds of PCR, any signal obtained from the mutant strand in later rounds will be obscured by background or by competing signal from amplification of ubiquitous wild-type strand.

An additional problem encountered in preparation of stool sample for detection of colorectal cancer is the difficulty of extracting sufficient quantities of relevant DNA from the stool. Stool samples routinely contain cell debris, enzymes, bacteria (and associated nucleic acids), and various other compounds that can interfere with traditional DNA extraction procedures and reduce DNA yield. Furthermore, DNA in stool often appears digested or partially digested, which can reduce the efficiency of extraction methods.

SUMMARY OF THE INVENTION

It has now been appreciated that the yield of nucleic acid from a stool sample is increased by providing an optimal ratio of solvent volume to stool mass in the sample. Accordingly, the invention provides stool sample preparation protocols for increasing sample nucleic acid yield.

In a preferred embodiment, methods of the invention comprise homogenizing a representative stool sample in a solvent in order to form a homogenized sample mixture having a solvent volume to stool mass ratio of at least 5:1, then enriching the homogenized sample for the target (human) DNA. The human DNA may then be analyzed for the characteristics of disease. Providing an optimal solvent volume to stool mass ratio increases the yield of nucleic acid obtained from the sample. An especially-preferred ratio of solvent volume to stool mass is between about 10:1 and about 30:1, more preferably from about 10:1 to about 20:1, and most preferably 10:1.

A preferred solvent for preparing stool samples according to the invention is a physiologically-compatible buffer such as a buffer comprising Tris-EDTA-NaCl. A preferred buffer is a Tris-EDTA-NaCl buffer comprising about 50 to about 100 mM Tris, about 10 to about 20 mM EDTA, and about 5 to about 15 mM NaCl at about pH 9.0. A particularly preferred buffer is 50 mM Tris, 16 mM EDTA and 10 mM NaCl at pH 9.0. Another preferred solvent is guanidine isothiocyanate (GITC). A preferred GITC buffer has a concentration of about 1 M to about 5 M. A particularly preferred GITC buffer has a concentration of about 3 M.

Also in a preferred embodiment, methods further comprise the step of enriching the homogenized sample mixture for human DNA by, for example, using sequence-specific nucleic acid probes hybridizing to target human DNA.

In an alternative preferred embodiment, the methods of the invention comprise homogenizing a stool sample in a physiologically-acceptable solvent for DNA in order to form a homogenized sample mixture having a solvent volume to stool mass ratio of at least 5:1; ensuring that the homogenized sample has at least a minimum number N of total DNA molecules to facilitate detection of a low-frequency target DNA molecule; and analyzing the target DNA for the characteristics of disease, preferably by amplifying the target DNA with a polymerase chain reaction.

In another embodiment, the present invention provides methods for analyzing DNA extracted from stool which comprise homogenizing a stool sample in a solvent for DNA in order to form a homogenized sample mixture having a solvent volume to stool mass ratio of at least 5:1; enriching the homogenized sample for human DNA; ensuring that the enriched homogenized sample has at least a minimum number N of total DNA molecules to provide for detection of a low-frequency target DNA molecule; and analyzing the target DNA for DNA characteristics indicative of disease.

Methods of the invention are useful to screen for the presence in a stool sample of nucleic acids indicative of colorectal cancer. Such methods comprise obtaining a representative stool sample (i.e., at least a cross-section); homogenizing the sample in a solvent having a solvent volume to stool mass ratio of at least 5:1; enriching the sample for target human DNA; and analyzing the DNA for characteristics of colorectal cancer. Various methods of analysis of DNA characteristics exist, such as those disclosed in co-owned, copending U.S. patent application Ser. No. 08/700,583, incorporated by reference herein.

Methods of the invention also comprise obtaining a representative (i.e., cross-sectional) sample of stool and homogenizing the stool in a buffer, such as a buffer comprising a detergent and a proteinase and optionally a DNase inhibitor.

The methods of the invention are especially and most preferably useful for detecting DNA characteristics indicative of a subpopulation of transformed cells in a representative stool sample. The DNA characteristics may be, for example, mutations, including point mutations, deletions, additions, translocations, substitutions, and loss of heterozygosity. Methods of the invention may further comprise a visual examination of the colon. Finally, surgical resection of abnormal tissue may be done in order to prevent the spread of cancerous or precancerous tissue.

Accordingly, methods of the invention provide means for screening for the presence of a cancerous or precancerous subpopulation of cells in a heterogeneous sample, such as a stool sample. Methods of the invention reduce morbidity and mortality associated with lesions of the colonic epithelium. Moreover, methods of the invention comprise more accurate and convenient screening methods than are currently available in the art, because such methods take advantage of the increased yield of relevant DNA.

Methods of the invention thus provide unexpected and enhanced detection and analysis of low-frequency DNA in a heterogeneous sample is facilitated through application of the methods described herein. That is, homogenization of stool sample in solvent at a ratio of at least 5:1 (volume to mass) alone, or in combination with methods for sample enrichment disclosed herein, provides a reliable method for obtaining a sufficient number of DNA molecules for effective and efficient analysis, even if the target molecule is a low-frequency DNA molecule. Further aspects and advantages of the invention are contained in the following detailed description thereof.

DETAILED DESCRIPTION OF THE INVENTION

The invention provides improved methods for extraction and analysis of nucleic acids from stool. According to methods of the invention, the yield of nucleic acids extracted from stool is increased by homogenizing the stool in a buffer at optimal ratio of buffer volume to stool mass. Yield is further improved by enriching for human DNA. Improved nucleic acid yields allow nucleic acid analysis of stool samples to be conducted more efficiently with less stool volume.

In preferred methods of the invention a stool sample obtained for analysis comprises at least a cross-section of a whole stool. As provided in U.S. Pat. No. 5,741,650, incorporated by reference herein, cells and cellular debris from the colonic epithelium is deposited onto and into stool in a longitudinal streak. Obtaining at least a cross-section of a stool ensures that a representative sampling of colonic epithelial cells and cellular debris is analyzed.

Once the stool sample is collected, it is homogenized in a physiologically acceptable solvent. A preferred means of homogenization employs agitation with glass beads. Physiologically acceptable solvents include those solvents generally known to those skilled in the art as suitable for dispersion of biological sample material. Such solvents include phosphate-buffered saline comprising a salt, such as 20–100 mM NaCl or KCl, and optionally a detergent, such as 1–10% SDS or Triton™, and/or a proteinase, such as proteinase K (at, e.g., about 20 mg/ml). A preferred solvent is a physiologically-compatible buffer comprising, for example, 1M Tris, 0.5M EDTA, 5M NaCl and water to a final concentration of 500 mM Tris, 16 mM EDTA and 10 mM NaCl at pH 9. The buffer acts as a solvent to disperse the solid stool sample during homogenization. Applicants have discovered that increasing the volume of solvent in relation to solid mass of the sample results in increased yields of DNA.

According to methods of the invention, solvent (buffer) is added to the solid sample in a solvent volume to solid mass ratio of at least about 5:1. The solvent volume to solid mass ratio is preferably in the range of about 10:1 to about 30:1, and more preferably in the range of about 10:1 to about 20:1. Most preferably, the solvent volume to solid mass ratio is about 10:1. Typically, solvent volume may be measured in milliliters, and solid mass measured in milligrams, but the practitioner will appreciate that the ratio of volume to mass remains constant, regardless of scale up or down of the particular mass and volume units. That is, solvent volume to solid mass ratios may be measured as liters:grams or μl: μg.

In a preferred embodiment of the present invention, the homogenized sample is enriched for the target (human) DNA. In the context of the present invention, "enrichment" of the sample means manipulating the sample to decrease the amount of undesired, non-human DNA in the sample relative to the amount of target human DNA. Enrichment techniques include sequence-specific capture of target DNA or removal of bacterial nucleic acids.

In a preferred embodiment of the invention, the enrichment step is carried out in a physiologically compatible buffer, such as guanidine isothiocyanate (GITC). Capture probes are then added to the mixture to hybridize to target DNA in order to facilitate selective removal of target DNA from the sample.

Sequence specific capture of target DNA can be accomplished by initially denaturing sample DNA to form single-stranded DNA. Then, a sufficient quantity of sequence specific oligonucleotide probe that is complementary to at least a portion of a target polynucleotide (e.g., a sequence in or near the p53 allele) is added. The probe sequence (labeled with biotin) is allowed to hybridize to the complementary target DNA sequence. Beads coated with avidin or streptavidin are then added and attach to the biotinylated hybrids by affinity-binding. The beads may be magnetized to facilitate isolation.

After separation of probe-target hybrids, the resultant DNA is washed repeatedly to remove inhibitors, including those commonly introduced via the capture probe technique. In the methods of the present invention, washes are preferably carried out approximately four times with 1M GITC and 0.1% detergent, such as Igepal (Sigma). The initial washes are then preferably followed by two washes with a standard wash buffer (such as Tris-EDTA-NaCl) to remove the GITC from the mix, since GITC is a known inhibitor of DNA polymerases, including those associated with PCR.

Finally, the target DNA is eluted into a small volume of distilled water by heating. Assays using polymerase chain reaction (PCR), restriction fragment length polymorphism (RFLP) analysis or other nucleic acid analysis methods may be used to detect DNA characteristics indicative of a disorder, such as colorectal cancer or pre-cancer. Several particularly useful analytical techniques are described in applications Ser. No. 08/700,583, U.S. Pat. No. 5,670,325, Ser. No. 08/815,576, abandoned and Ser. No. 08/877,333, U.S. Pat. No. 5,888,778, the disclosures of which are incorporated herein by reference.

In an alternative embodiment, the homogenized sample is examined to determine that the sample has at least a minimum number (N) of total DNA molecules to provide for detection of a low-frequency target DNA molecule. The number of molecules analyzed in a sample determines the ability of the analysis to detect low-frequency events. In the case of PCR, the number of input molecules must be about 500 if the PCR efficiency is close to 100%. As PCR efficiency goes down, the required number of input molecules goes up. Analyzing the minimum number of input molecules reduces the probability that a low-frequency event is not detected in PCR because it is not amplified in the first few rounds. Methods of the invention therefore include determining a threshold number of sample molecules that must be analyzed in order to detect a low-frequency molecular event at a prescribed level of confidence.

As is more fully described in U.S. Ser. No. 60/109,567, filed Nov. 23, 1998, which is incorporated herein by reference, the determination of a minimum number N of DNA molecules that must be present in a sample to permit amplification and analysis of a low-frequency target DNA molecule is based upon a model of stochastic processes in PCR. Utilizing pre-set or predetermined values for PCR efficiency and mutant DNA to wild-type DNA ratio in the sample, the model predicts the number of molecules that must be presented to the PCR in order to ensure, within a defined level of statistical confidence, that a low-frequency molecule will be amplified.

The skilled practitioner will appreciate that determination of the minimum number N of molecules present in the sample may be used in lieu of, or in addition to, the enrichment techniques detailed above, to ensure reliable results in the methods of the present invention.

Alternatively, methods of the invention may also be used to isolate total DNA from stool homogenate. The homogenized mixture is centrifuged to form a pellet made up of cell debris and stool matter, and a supernatant containing nucleic acid and associated proteins, lipids, etc. The supernatant is treated with a detergent, such as 20% SDS, and enzymes capable of degrading protein (e.g., Proteinase K). The supernatant is then Phenol-Chloroform extracted. The resulting purified nucleic acids are then precipitated by means known in the art. A variety of techniques in the art can then be employed to manipulate the resulting nucleic acids, including further purification or isolation of specific nucleic acids.

Methods of the invention are also useful for analysis of pooled DNA samples. As described in more detail in application Ser. No. 09/098,180, abandoned, and U.S. Pat. No. 5,670,325, both of which are incorporated by reference herein, enumerative analysis of pooled genomic DNA samples is used to determine the presence or likelihood of disease. Pooled genomic DNA from healthy members of a population and pooled genomic DNA from diseased members of a population are obtained. The number or amount of each variant at a single-nucleotide polymorphic site is determined in each sample. The numbers or amounts are analyzed to determine if there is a statistically-significant difference between the variant(s) present in the sample obtained from the healthy population and those present in the sample obtained from the diseased population. A statistically-significant difference indicates that the polymorphic locus is a marker for disease.

These methods may be used to identify a nucleic acid (e.g., a polymorphic variant) associated with a disease. Such methods comprise counting the number or determining the amount of a nucleic acid, preferably a single base, in members of a diseased population, and counting numbers or determining amounts of the same nucleic acid in members of a healthy population. A statistically-significant difference in the numbers of the nucleic acid between the two populations is indicative that the interrogated locus is associated with a disease.

Once the polymorphic locus is identified, either by methods of the invention or by consulting an appropriate database, such methods are useful to determine which variant at the polymorphic locus is associated with a disease. In this case, enumerative methods are used to determine whether there is a statistically-significant difference between the number of a fist variant in members of a diseased population, and the number of a second variant at the same locus in members of a healthy population. A statistically-significant difference is indicative that the variant in members of the diseased population is useful as a marker for disease. Using this information, patients are screened for the presence of the variant that is thought to be associated with disease, the presence such a variant being indicative of the presence of disease, or a predisposition for a disease.

Methods of the present invention are particularly useful for isolation and analysis of nucleic acids that encompass genes that have mutations implicated in colorectal cancer, such as kras. The kras gene has a length of more than 30 kbp and codes for a 189 amino acid protein characterized as a low-molecular weight GTP-binding protein. The gene acquires malignant properties by single point mutations, the most common of which occurs at the 12th amino acid. Several studies have confirmed that approximately 40% of primary colorectal adenocarcinoma cells in humans contain a mutated form of the kras gene. Accordingly, the kras gene is a particularly suitable target for the methods of colorectal cancer detection of the present invention.

Toward this end, applicants have constructed a suitable exemplary capture probe directed to the kras nucleotide sequence. The capture probe, designated CP1, has the following sequence: 5' GCC TGC TGA AAA TGA CTG AAT ATA AAC TTG TGG TAG T 3' (SEQ, ID NO: 1), and is preferably biotinylated at the 5' end in order to facilitate isolation. As illustrated more fully below, CP1 is effective in the sequence specific capture of kras DNA.

Figure 1:
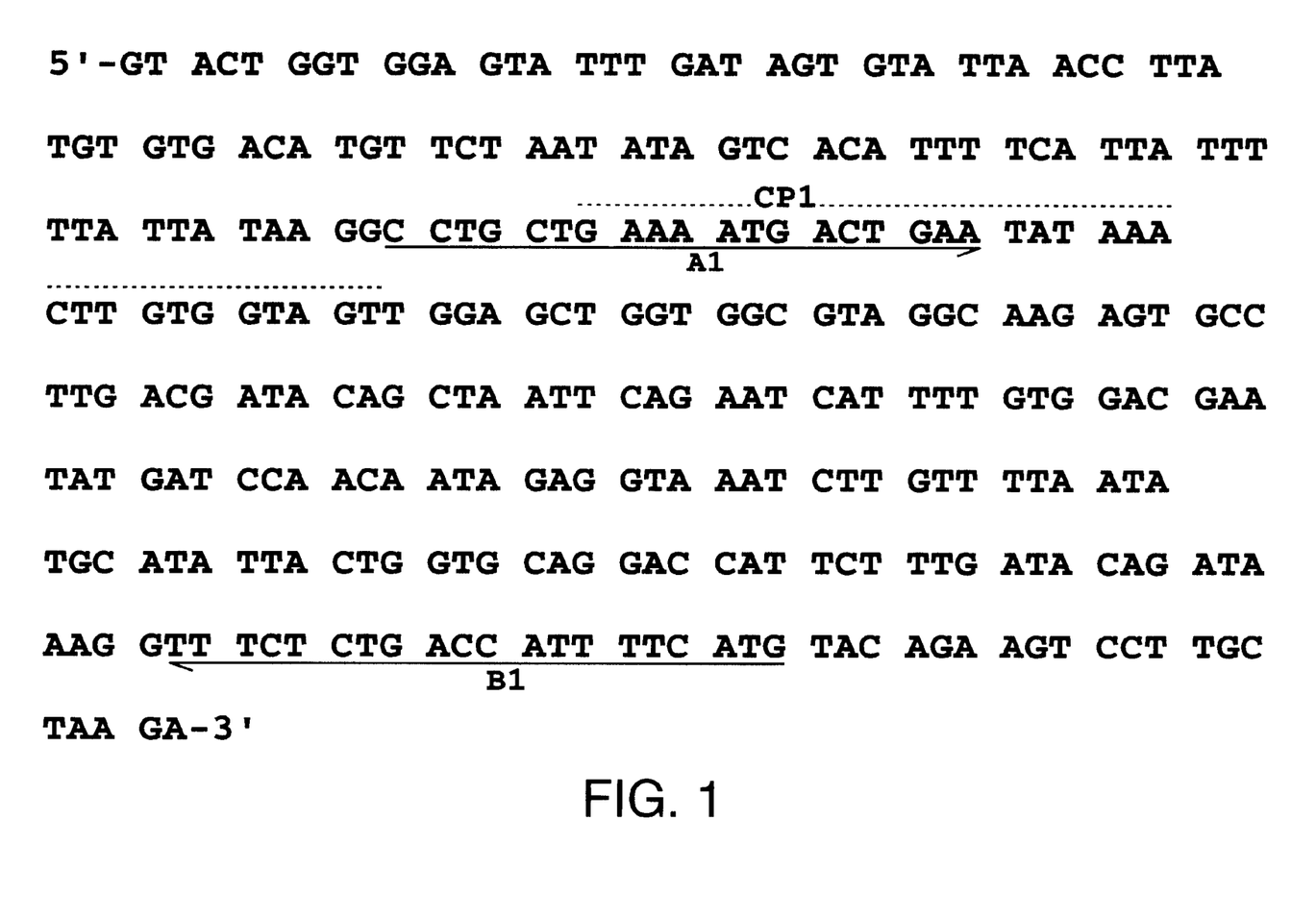
FIG. 1 is a representation of a partial nucleotide sequence of the kras gene (base pairs 6282–6571) and the positions of capture probe CP1, PCR primer A1, and PCR primer B1, in relation to the kras nucleotide sequence.

Suitable PCR primers for the analysis of extracted kras DNA sequence have also been determined. Primer A1 has the sequence: 5' C CTG CTG AAA ATG ACT GAA 3' (SEQ ID NO: 2), and Primer B1 has the sequence: 5' CAT GAA AAT GGT CAG AGA AA 3' (SEQ ID NO: 3). The PCR primers A1 and B1, as well as capture probe CP1, are depicted in FIG. 1, showing their relation to the kras nucleotide sequence, base pairs 6282–6571 (SEQ ID NO: 4). One skilled in the art can construct other suitable capture probes and PCR primers for kras or other target genes or nucleotide sequences, using techniques well known in the art.

Accordingly, the methods of the present invention, which involve homogenizing stool sample in a volume of solvent such that the ratio of solvent volume to stool mass is at least 5:1, and/or enriching the sample for human DNA, provide a means for obtaining a sample having a minimum number N of total DNA molecules to facilitate detection of a low-frequency target DNA molecule. These methods thus provide the unexpected result that one is now able to reliably detect a small portion of low-frequency DNA in a heterogeneous sample.

The following examples provide further details of methods according to the invention. However, numerous additional aspects of the invention will become apparent upon consideration of the following examples.

EXAMPLE 1
Stool Sample Preparation

Voided stool was collected from a patient and a cross-sectional portion of the stool was removed for use as a sample. After determining the mass of the sample, an approximately 10×volume of Tris-EDTA-NaCl lysis buffer was added to the solid sample in a test tube. The final concentration of the buffer was 500 mM Tris, 16 mM EDTA and 10 mM NaCl, at a pH of about 9.0. Four 10 mm glass balls were placed in the tube and the tube and contents were homogenized in an Exactor II shaker for 15 minutes. The homogenized mixture was then allowed to stand 5 minutes at room temperature. The tube was then centrifuged for 5 minutes at 10,000 rpm in a Sorvall Centrifuge, and the supernatant was transferred to a clean test tube. A 20% SDS solution was added to the tube to a final concentration of 0.5%. Proteinase K was also added to the tube to a final concentration of 500 mg/ml. The tube was then incubated overnight at 37° C.

After incubation, the contents of the tube were extracted with an equal volume of phenol/chloroform and centrifuged at 3500 rpm for 3 minutes. The aqueous layer was then transferred to a new tube and extracted three (3) times with equal volumes of chloroform and centrifuged at 3500 rpm for 3 minutes. The aqueous layer was then transferred to a new tube and 0.1×volume of 3M NaOAc was added to the aqueous portion, which was then extracted with an equal volume of isopropanol, and centrifuged for 5 minutes at 12,000 rpm. The supernatant was discarded, and the pellet was washed with 10 ml of 70% ethanol, and centrifuged at 12,000 rpm for 5 minutes. The supernatant was discarded and the pellet containing isolated DNA was dried by inverting the tube.

EXAMPLE 2

A comparative analysis of solvent volume to mass ratios was conducted. Three separate stool samples were prepared as described above. A first sample, designated SS88-3x, was homogenized in buffer at a volume to mass ratio of 3:1. A second sample, designated SS88-5x, was homogenized at a ratio of 5:1; and a third sample, designated SS88-10x, was homogenized at a ratio of 10:1.

Figure 2:
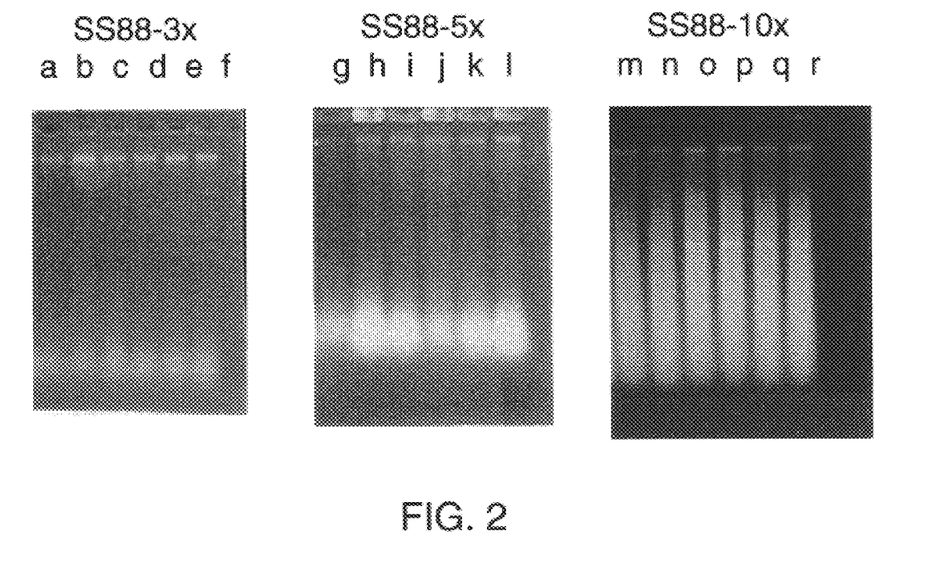
FIG. 2 is an image produced using a Stratagene Eagle Eye II Still Video System (Stratagene, La Jolla, Calif.), of the results of a gel electrophoresis run with the uncut DNA extracted as described in Example 2.

Total DNA from each sample was resuspended in 100 ul of 100 mM Tris, 10 mM EDTA buffer and 10 ul aliquots were loaded onto a 4% agarose gel for electrophoresis at 125 V constant voltage for about one hour. The results are shown in FIG. 2. As shown in FIG. 2, the yield of total DNA increased as the ratio of solvent to mass increased from 3× to 10×.

EXAMPLE 3

A second set of four equivalent samples was prepared from a single stool sample. Each of the four samples was of equal mass, and was homogenized as described in Example 1 at a solvent volume to stool mass ratio of 5:1, 10:1, 20:1, and 30:1, respectively. After homogenization each sample was subdivided into 8 aliquots, 4 treated with RNase, and 4 untreated. Total DNA was then isolated as described above and analyzed on agarose gels.

Figure 3:
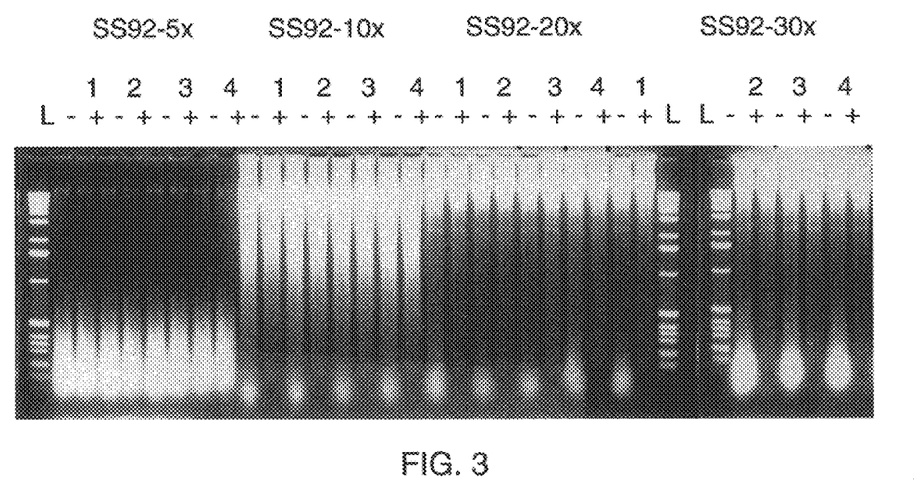
FIG. 3 is an image produced using a Stratagene Eagle Eye II Still Video System (Stratagene, La Jolla, Calif.), of the results of a gel electrophoresis run with the DNA extracted as described in Example 3.

The results are shown in FIG. 3. As shown, a ratio of 10:1 produced the greatest yield of nucleic acids. FIG. 3 also shows the effect of RNase treatment on the yield of DNA from each stool sample. As shown in the Figure, RNase treatment virtually eliminates RNA from the sample, but leaves DNA intact. The results indicate that optimal solvent volume to stool mass ratios greatly increase DNA yield from stool samples.

EXAMPLE 4
Sequence-Specific Capture of target DNA

Once extracted from stool, specific nucleic acids are isolated using sequence-specific capture probes. Total DNA was extracted from a stool sample according to the methods described in Example 1. The pelletized DNA was resuspended in 1 ml of TE buffer. A 100 $\mu$l aliquot of this solution was removed to a new tube and 100 $\mu$l of 6M guanidine isothiocyanate (GITC) was added to a final concentration of 3M GITC. A vast excess of biotinylated kras capture probe CP1 was the added to the sample. The mixture was heated to 95° C. for 5 minutes to denature the DNA, then cooled to 37° C. for 5 minutes. Finally, probe and target DNA were allowed to hybridize for 30 minutes at room temperature. Streptavidin-coated magnetized beads (320 mg) (Dynal Corp.) were suspended in 400 $\mu$l distilled water and added to the mixture. After briefly mixing, the tube was maintained at room temperature for 30 minutes.

Once the affinity binding was completed, a magnetic field was applied to the sample to draw the magnetized isolation beads (both with and without hybridized complex out of the sample. The beads were then washed four (4) times in 1M GITC/0.1% Igepal (Sigma, St. Louis, Mo.) solution for 15 minutes, followed by two (2) washes with wash buffer (TE with 1M NaCl) for 15 minutes in order to isolate complexed streptavidin. Finally, 10 $\mu$l distilled water was added to the beads and heated at 95° C. for 3 minutes to elute the DNA. Sequencing and/or gel electrophoresis enable confirmation of the capture of kras-specific DNA.

Accordingly, methods of the invention produce increased yields of DNA from stool, thereby allowing more efficient sequence-specific capture of target nucleic acid. Methods of the invention provide improvements in the ability to detect disease-related nucleic acid mutations present in stool. The skilled artisan will find additional applications and embodiments of the invention useful upon inspection of the foregoing description of the invention. Therefore, the invention is limited only by the scope of the appended claims.

What is claimed is:

1. A method for analyzing DNA extracted from stool, comprising:

homogenizing a stool sample in a solvent for DNA in order to form a homogenized sample mixture having a solvent volume to stool mass ratio of at least 5:1;

enriching said homogenized sample for human DNA; and analyzing said human DNA for characteristics of disease.

2. The method of claim 1 wherein the solvent volume to stool mass ratio is from about 10:1 to about 30:1.

3. The method of claim 2 wherein the solvent volume to stool mass ratio is about 10:1 to about 20:1.

4. The method of claim 2 wherein the solvent volume to stool mass ratio is about 10:1.

5. The method of claim 1 wherein the solvent comprises a buffer that disperses biological material.

6. The method of claim 1 wherein said enriching step comprises contacting said DNA with a sequence-specific capture probe.

7. The method of claim 1 wherein said solvent comprises a detergent and a proteinase.

8. The method of claim 1 wherein said DNA is human DNA.

9. A method of screening for the presence of a colorectal cancerous or pre-cancerous lesion in a patient, the method comprising the steps of:
   obtaining a sample comprising at least a cross-sectional portion of a stool voided by the patient;
   homogenizing the sample in a solvent in order to form a homogenized sample mixture having a solvent volume to stool mass ratio of at least 5:1;
   enriching said sample for a target human DNA; and
   analyzing the target human DNA for DNA characteristics indicative of the presence of said colorectal cancerous or pre-cancerous lesion.

10. The method of claim 9 wherein said analyzing step comprises amplifying the DNA with a polymerase chain reaction.

11. The method of claim 9 wherein said DNA characteristics comprise a loss of heterozygosity encompassing a polymorphic locus.

12. The method of claim 9 wherein said DNA characteristic is a mutation.

13. The method of claim 12 wherein said mutation is selected from the group consisting of loss of heterozygosity and microsatellite instability.

14. The method of claim 9 wherein said DNA characteristics comprise a deletion in a tumor suppressor allele.

15. The method of claim 9 wherein said analyzing step comprises determining whether a difference exists in said sample between a number X of a first allele known or suspected to be mutated in a subpopulation of cells in the sample and a number Y of a second allele that is known or suspected not to be mutated in a subpopulation of cells in the sample, the presence of a statistically-significant difference being indicative of a mutation in a subpopulation of cells in the sample and the potential presence of a cancerous or precancerous lesion.

16. The method of claim 9 wherein said analyzing step comprises determining whether a difference exists between a number of a target tumor suppressor allele in the sample and a number of a non-cancer-associated reference allele in the sample, the presence of a statistically-significant difference being indicative of a deletion of the target tumor suppressor allele in a subpopulation of cells in the sample and the potential presence of a cancerous or precancerous lesion.

17. The method of claim 9 wherein said analyzing step further comprises the steps of:
   a) detecting an amount of a maternal allele at a polymorphic locus in the sample;
   b) detecting an amount of a paternal allele at the polymorphic locus in the sample; and
   c) determining whether a difference exists between the amounts of maternal and paternal allele,
   the presence of a statistically-significant difference being indicative of a deletion at the polymorphic locus in a subpopulation of cells in the sample and the potential presence of a lesion.

18. The method of claim 17 wherein said polymorphic locus is a single base polymorphism and is heterozygous between said maternal and paternal alleles.

19. The method of claim 17 wherein said detecting steps comprise,
   a) hybridizing probe to a portion of said polymorphic locus on both maternal and paternal alleles that is immediately adjacent to said single-base polymorphism;
   b) exposing said sample to a mixture of detectably-labeled dideoxy nucleoside triphosphates under conditions which allow appropriate binding of said dideoxy nucleoside triphosphates to said single-base polymorphism;
   c) washing the sample; and
   d) counting an amount of each detectably-labeled dideoxy nucleoside triphosphate remaining for the sample.

20. The method of claim 19 wherein said detectable label is selected from the group consisting of radioisotopes, fluorescent compounds, and particles.

21. The method of claim 9 wherein said analyzing step comprises a method for detecting heterozygosity at a single-nucleotide polymorphic locus, comprising the steps of:
   a) hybridizing probes to a sequence immediately adjacent to a single-base polymorphism;
   b) exposing the sample to a plurality of different labeled dideoxy nucleotides
   c) washing the sample;
   d) determining which of said dideoxy nucleotides are incorporated into said probes; and
   e) detecting heterozygosity at the single-nucleotide polymorphic site as the detection of two dideoxy nucleotides having been incorporated into the probe.

22. The method of claim 9 wherein said analyzing step comprises:
   (a) exposing the sample to a plurality of a first oligonucleotide probe and to a plurality of a second oligonucleotide probe under hybridization conditions, thereby to hybridize
      (1) said first oligonucleotide probes to copies of a first polynucleotide segment characteristic of wild-type cells of the organism, and
      (2) said second oligonucleotide probes to copies of a second polynucleotide segment characteristic of a wild-type genomic region suspected to be deleted or mutated in colorectal cancer cells;
   (b) detecting a first number of duplexes formed between said first probe and said first segment and a second number of duplexes formed between said second probe and said second segment; and
   (c) determining whether there is a difference between the number of duplexes formed between said first probe and said first segment and the number of duplexes formed between said second probe and said second segment,
   the presence of a statistically-significant difference being indicative of the presence in said sample of a colorectal cancer or precancerous lesion.

23. The method of claim 22 wherein said first and second oligonucleotide probes each are coupled to a distinct detectable label.

24. The method of claim 22 wherein
   said first oligonucleotide probes are attached to a first particle in a ratio of one first oligonucleotide probe to one particle and said second oligonucleotide probes are attached to a second particle detectably distinct from said first particle in a ratio of one second oligonucleotide probe to one second particle, wherein said detecting step comprises separating hybridized from unhybridized first and second oligonucleotide probes and subsequently passing hybridized first and second oligonucleotide probes through a detector to determine said first and second numbers.

25. The method of claim 24 wherein said first and second particles are of detectably different sizes.

26. The method of claim 24 wherein said first and second particles are of detectably different colors.

27. The method of claim 22 further comprising, prior to step a) the steps of converting double-stranded DNA in said sample to single-stranded DNA and removing complement to said first and second polynucleotide segments.

28. The method of claim 27 wherein said removing step comprises hybridizing said complement to a nucleic acid probe attached to a magnetic particle and subsequently removing said magnetic particle from the sample.

29. The method of claim 9 wherein said analyzing step comprises a method for detecting a nucleic acid sequence change in a target allele in the sample, comprising the steps of:

(a) determining
    (i) an amount of wild-type target allele in the sample, and
    (ii) an amount of a reference allele in the sample; and
(b) detecting a nucleic acid sequence change in the target allele in the sample,
a statistically significant difference in the amount wild-type target allele and the amount of reference allele obtained in said determining step being indicative of a nucleic acid sequence change.

30. The method according to claim 29 wherein said determining step comprises exposing said sample to a first oligonucleotide probe capable of hybridizing with a portion of said wild-type allele and to a second oligonucleotide probe capable of hybridizing to a portion of said reference allele, and removing from said sample any unhybridized first or second oligonucleotide probe.

31. A method for screening for the presence of a colorectal cancerous or precancerous lesion in a patient, the method comprising the steps of:

obtaining a sample comprising at least a cross-sectional portion of a stool voided by the patient;

homogenizing the sample in a solvent in order to form a homogenized sample mixture having a solvent volume to stool mass ratio of at least 5:1;

determining if said sample has at least a minimum number N of total DNA molecules to provide for detection of a low-frequency target DNA molecule;

analyzing the target DNA for DNA characteristics indicative of the presence of said colorectal cancerous or pre-cancerous lesion.

32. A method for screening for the presence of a colorectal cancerous or precancerous lesion in a patient, the method comprising the steps of:

obtaining a sample comprising at least a cross-sectional portion of a stool voided by the patient;

homogenizing the sample in a solvent in order to form a homogenized sample mixture having a solvent volume to stool mass ratio of at least 5:1;

enriching said homogenized sample for target human DNA;

determining if said sample has at least a minimum number N of total DNA molecules to provide for detection of a low-frequency target DNA molecule;

analyzing the target human DNA for DNA characteristics indicative of the presence of said colorectal cancerous or pre-cancerous lesion.

33. The method of claim 31 wherein said analyzing step comprises amplifying the DNA with a polymerase chain reaction.

34. The method of claim 32 wherein said analyzing step comprises amplifying the DNA with a polymerase chain reaction.

35. The method of claim 32 wherein said enriching step comprises contacting said DNA with a sequence-specific capture probe.

36. The method of claim 1 wherein the solvent comprises between about 10 mM EDTA and about 20 mM EDTA.

37. The method of claim 1 wherein the solvent comprises about 16 mM EDTA.

38. The method of claim 9 wherein the solvent comprises between about 10 mM EDTA and about 20 mM EDTA.

39. The method of claim 9 wherein the solvent comprises about 16 mM EDTA.

40. The method of claim 31 wherein the solvent comprises between about 10 mM EDTA and about 20 mM EDTA.

41. The method of claim 31 wherein the solvent comprises about 16 mM EDTA.

42. The method of claim 32 wherein the solvent comprises between about 10 mM EDTA and about 20 mM EDTA.

43. The method of claim 32 wherein the solvent comprises about 16 mM EDTA.

44. The method of claim 5 wherein the buffer comprises Tris-EDTA-NaCl.

45. The method of claim 44 wherein the Tris-EDTA-NaCl buffer comprises a final concentration of about 50 mM Tris, about 16 mM EDTA and about 10 mM NaCl at about pH 9.0.

46. The method of claim 1 wherein the solvent comprises guanidine isothiocyanate buffer.

47. The method of claim 46 wherein the guanidine isothiocyanate buffer comprises a final concentration of from about 1 to about 5 M.

48. The method of claim 47 wherein the guanidine isothiocyanate buffer comprises a final concentration of about 3 M.

* * * * *